United States Patent
Ahmad et al.

(10) Patent No.: US 6,667,053 B1
(45) Date of Patent: *Dec. 23, 2003

(54) D AND L ETHERLIPID STEREOISOMERS AND LIPOSOMES

(75) Inventors: Imran Ahmad, Cranbury, NJ (US); Eric Mayhew, Seattle, WA (US); Andrew Janoff, Yardley, PA (US)

(73) Assignee: Elan Pharmaceuticals, Inc., S. San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/540,050

(22) Filed: Mar. 31, 2000

Related U.S. Application Data

(63) Continuation-in-part of application No. 09/390,395, filed on Sep. 3, 1999, now Pat. No. 6,180,137, which is a continuation of application No. 09/017,440, filed on Feb. 2, 1998, now Pat. No. 5,965,159, which is a continuation-in-part of application No. 08/602,669, filed on Feb. 16, 1996, now Pat. No. 5,762,958.

(51) Int. Cl.$^7$ .......................... A61K 9/133; A61K 9/127
(52) U.S. Cl. ................................ 424/450; 428/402.2
(58) Field of Search ................. 424/450, 1.21, 424/9.321, 9.51, 417, 94.3; 436/829; 935/54; 428/402.2

(56) References Cited

U.S. PATENT DOCUMENTS

| | | | |
|---|---|---|---|
| 3,752,886 A | 8/1973 | Munder et al. ............. 424/199 |
| 4,159,988 A | 7/1979 | Eibl et al. ................. 260/340.9 |
| 4,163,748 A | 8/1979 | Eibl et al. .................... 260/403 |
| 4,382,035 A | 5/1983 | Eibl ............................ 260/403 |
| 4,734,225 A | 3/1988 | Eibl ............................ 260/386 |
| 4,804,789 A | 2/1989 | Eibl ............................ 568/853 |
| 4,920,016 A | 4/1990 | Allen et al. ................. 424/450 |
| 4,965,391 A | 10/1990 | Counsell et al. ............. 558/169 |
| 4,983,397 A | 1/1991 | Schroit et al. .............. 424/450 |
| 5,013,556 A | 5/1991 | Woodle et al. .............. 424/450 |
| 5,436,234 A | 7/1995 | Eibl .............................. 514/77 |
| 5,762,958 A | 6/1998 | Mayhew et al. ............. 424/450 |
| 5,932,242 A | 8/1999 | Franklin et al. | |
| 5,965,159 A | 10/1999 | Mayhew et al. | |
| 6,007,839 A | 12/1999 | Mayhew et al. | |
| 6,017,557 A | 1/2000 | Franklin et al. | |

FOREIGN PATENT DOCUMENTS

| | | | |
|---|---|---|---|
| DE | 4132345 | 4/1993 | ......... A61K/31/685 |
| DE | 4408011 | 11/1995 | ......... A61K/31/685 |
| GB | 1583661 | 1/1981 | .......... A61K/31/66 |
| JP | 61-22020 | 1/1986 | |
| JP | 072294 | 7/1986 | |
| WO | 93/04673 | 3/1993 | .......... A61K/9/127 |
| WO | 93/08202 | * 4/1993 | |
| WO | 94/27580 | 12/1994 | .......... A61K/9/127 |

OTHER PUBLICATIONS

Mende et al., "Effect of ET–18–OCH$_3$/Cholesterol Liposomes on the Membrane Potential of Isolated Endothelial Cells," *Pharmazie* 44(2):(1989). (With English translation.).

Baker, Int. J. Immuno Pharm, 13(4), p395, 1991.

(List continued on next page.)

*Primary Examiner*—Gollamudi S. Kishore

(57) ABSTRACT

A liposome having a lipid bilayer, where the lipid bilayer includes either the L or D stereoisomer of an ether lipid or a non-equal mixture of both. Most preferably the liposome also comprises (a) an underivatized phosphatidylcholine; (b) a sterol; (c) about 5–20 mole % of a phosphatidylethanolamine linked to a dicarboxylic acid at the ethanolamine group of the phosphatidylethanolamine, and (d) greater than about 10 mole % to less than about 30 mole % of either the L or D stereoisomer of an ether lipid. The liposome may be used as an anti-cancer or anti-inflammatory agent.

24 Claims, 9 Drawing Sheets

OTHER PUBLICATIONS

Bazill, et al., "Role of Endocytosis in the Action of Ether Lipids on WEHI–3B, HL60, and FEDCP–Mix A4 Cells", Cancer Res. 50: 7505 (1990).

Berdel, "Membrane–interactive lipids as experimental anticancer drugs", Br. J. Cancer 64: 208 (1991).

Berdel, "Ether Lipids and Derivatives as Investigational Anticancer Drugs", Onkologie 13: 245 (1990).

Bhatia, et al., "Sterospecific Systhesis on Antitumor Active Thioether PAF Analogs", Lipids 26(12): 1424 (1991).

Blume et al, "Specific targeting with poly(ethylene glycol)–modified liposomes: coupling of homing devices to the ends of the polymeric chains combines effective target binding with long circulation times" Biochim. Biophys. Acta. 1149: 180–184 (1993).

Daicho, et al., "Effects of alkyl glycosides incorporated into liposomes prepared from synthetic amphiphiles on their tissue distribution in Ehrlich solid tumor–bearing mice", BBA, 1107:61 (1992).

Darnell et al., *Molecular Cell Biology*, Scientific American Books, Inc. (1986), New York, pp. 573–575.

Deamer and Uster, "Lipsome Preparation: Methods and Mechanism," in: *Liposomes* (M. Ostro, ed.), Marcel Dekker, Inc., New York (1983), pp. 27–52.

Dietzfelbinger et al., "Removal of Breast Cancer Cells from Bone Marrow by in Vitro Purging with Ether Lipids and Cryopreservation", Cancer Res. 53: 3747 (1993).

Dive, et al., "Multiparametric Flow Cytometry of the Modulation of Tumore Cell Membrane Permeability by Developmental Antitumore Ether Lipid SRI 62–834 in EMT6 Mouse Mammary Tumor and HL–60 Human Promyelocytic Leukemia Cells", Cancer Res., 51:799 (1991).

Gabizon et al., "Prolongation of Circulation Time of Doxorubicin Encapsulated in Liposomes Containing a Polyethylene Glycol–Derivatived Phospholipid: Pharmacokinetic Studies in Rodents and Dogs", Pharm. Res. 10(5): 703 (1993).

Kaufmann–Kolle, et al., "Liposomal Hexadecylphosphocholine (HEPC): in Vitro and in Vivo Application", Chemical Abs. V4,10.08.

Kuchera, AIDS Res. & Human Retrovirues, 6(4), p491, 1990.

Layton et al., "The Interaction of Liposomes with Cells: The Relation of Cell Specific Toxicity to Lipid Composition", Eur. J. Cancer 16: 64 (1980).

Lewis and McElhaney, "The Mesomorphic Phase Behavior of Lipid Bilayers," in *The Structure of Biological Membranes* (P. Yeagle, ed.), CRC Press, Inc. (1992), Boca Raton, Fl., pp. 73–155, at pp. 123–126.

Muschiol et al., "Alkyl Phosphocholine: Toxicity and Anticancer Properties", Lipids 22(11): 930 (1987).

Nairn, in: *Remington's Pharmaceutical Science* (A. Gennaro, ed.), Mack Publishing Co., Easton, PA, (1985), pp. 1492–1517.

Park et al., "Some negatively charged phopholipid derivatives prolong the liposome circulation in vivo", Biochim. Biophys. Acta. 1108: 257 (1992).

Powis et al., "Selective Inhibition of Phophatidylinositol Phospholipase C by Cytotoxic Ether Lipid Analogues", Cancer Res. 52: 2835 (1992).

Reed et al., "Antineoplastic Ether–Linked Phopholipid induces differentiation of acute myelogenous leukemic KG–1 cells into marcophase–like cells", Life Sci. 49: 1221 (1991).

Runge et al., "Destruction of Human Solid Tumors by Alkyl Lysophopholipids", JNCI. 64(6): 1301 (1980).

Tritton, et al., "How to Kill Cancer Cells: Membranes and Cell Signaling as Targets in Cancer Chemotherapy", Cancer Cells 2(4): 95 (1990).

Workman, "Antitumor Ether Lipids: Endocytosis as a Determinant of Cellular Sensitivity", Cancer Cells 3(8): 315 (1991).

Workman et al., "Plastelet–activating factor (PAF) antagonist WEB 2086 does not modulate the cytotoxicity of PAF or antitumour alkyl lysophospholipids ET–18–O–Methyl and SRIU 62–834 in HL–60 promyelocytic leukaemia cells", Biochem. Pharmacol. 41(2): 319 (1991).

Zeisig et al., "Antineoplastic activity in vitro of free and liposomal alkylphophocholines;", Anti–Cancer Drugs 4: 57 (1993).

* cited by examiner

FIG. 1A

Stereospecific synthesis of L-ET18OCH$_3$

Step 1: Formation of n-Octadecylmesylate

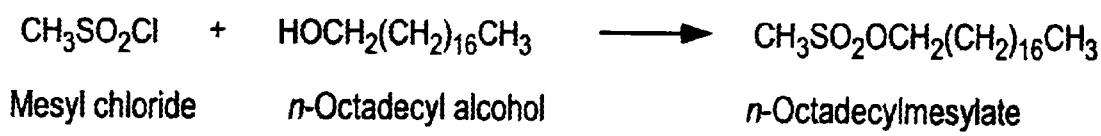

CH$_3$SO$_2$Cl   +   HOCH$_2$(CH$_2$)$_{16}$CH$_3$   ⟶   CH$_3$SO$_2$OCH$_2$(CH$_2$)$_{16}$CH$_3$
Mesyl chloride    n-Octadecyl alcohol                n-Octadecylmesylate Step 2a: Coupling of the chiral synthon with n-Octadecyl alcohol

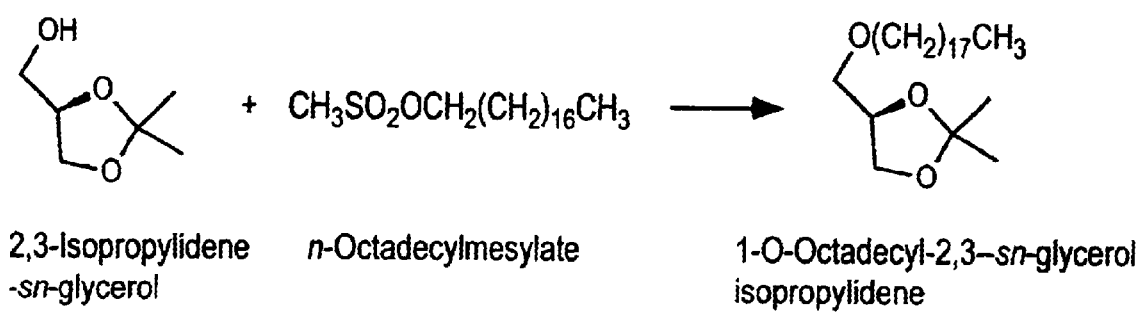

2,3-Isopropylidene    n-Octadecylmesylate           1-O-Octadecyl-2,3-sn-glycerol
-sn-glycerol                                         isopropylidene Step 2b: Deprotection of hydroxyl groups

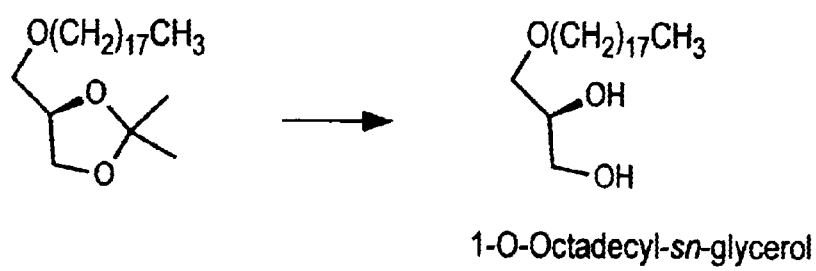

1-O-Octadecyl-sn-glycerol

FIG. 1B
Step 3: Protection of primary hydroxyl Group
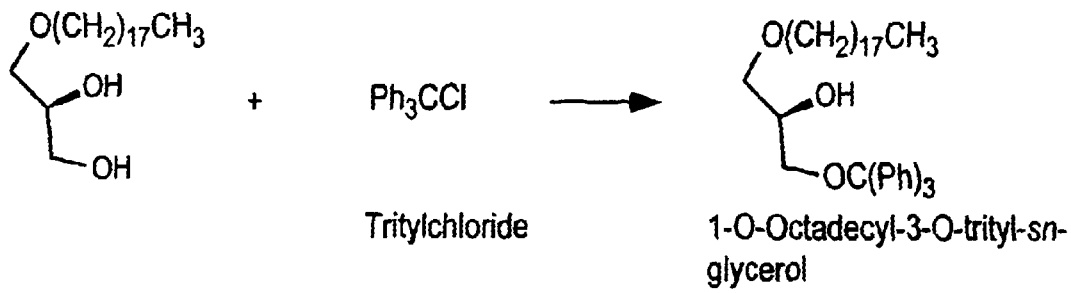
Tritylchloride        1-O-Octadecyl-3-O-trityl-sn-glycerol
Step 4a: Methylation of Secondary Hydroxyl Group
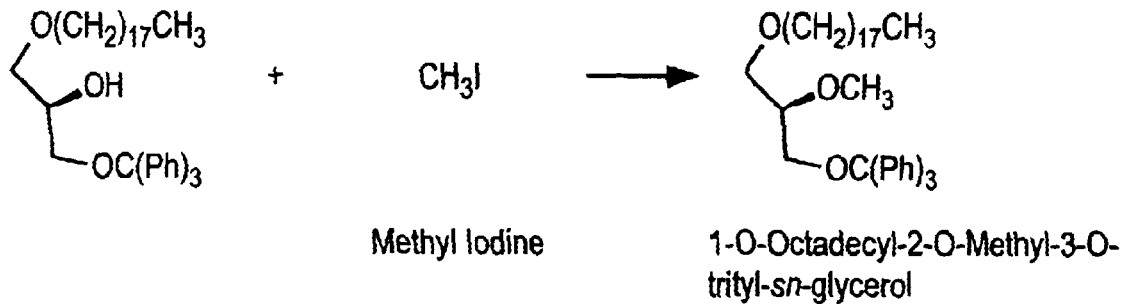
Methyl Iodine        1-O-Octadecyl-2-O-Methyl-3-O-trityl-sn-glycerol
Step 4b: Deprotection of Primary Hydroxyl Group
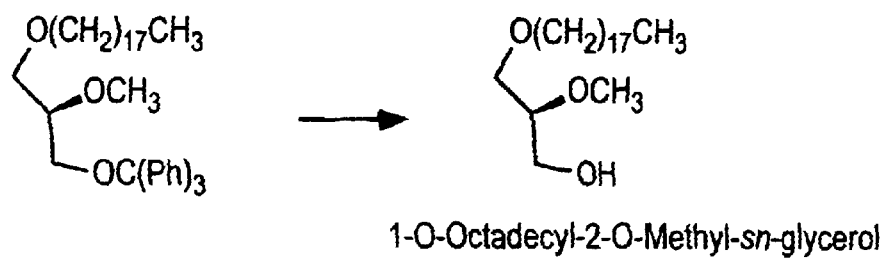
1-O-Octadecyl-2-O-Methyl-sn-glycerol

FIG. 1C
Step 5a: Formation of Phospho-ester bond
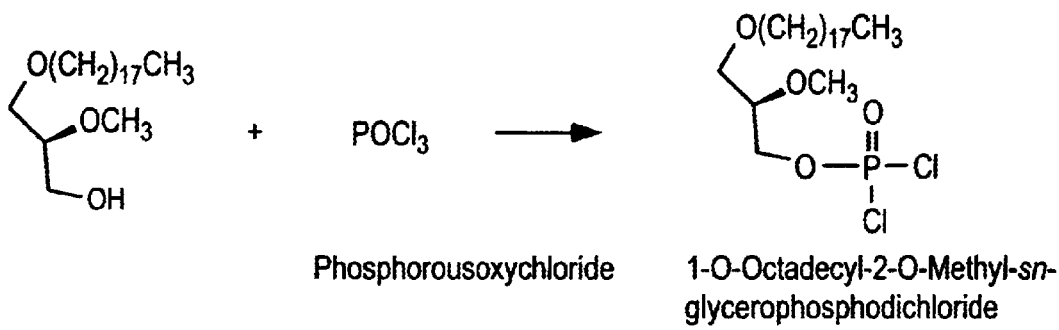
Phosphorousoxychloride      1-O-Octadecyl-2-O-Methyl-*sn*-glycerophosphodichloride
Step 5b: Coupling with Choline Tosylate
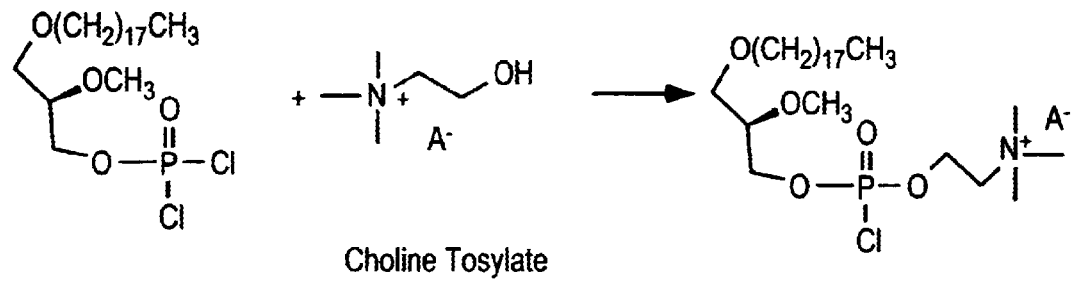
Choline Tosylate
Step 5c: Formation of Phosphocholine to complete synthesis
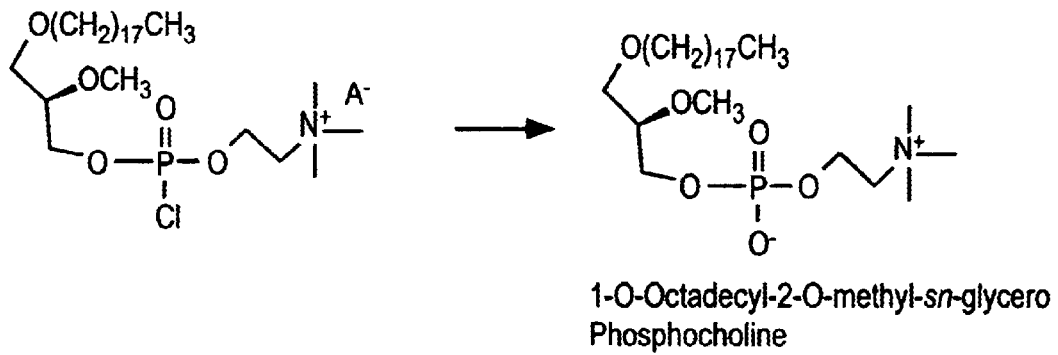
1-O-Octadecyl-2-O-methyl-*sn*-glycero Phosphocholine L-EL and D-EL Induce Similar
Changes in U-937 Cell Cycle (48 hrs)
■ L-EL
□ D-EL
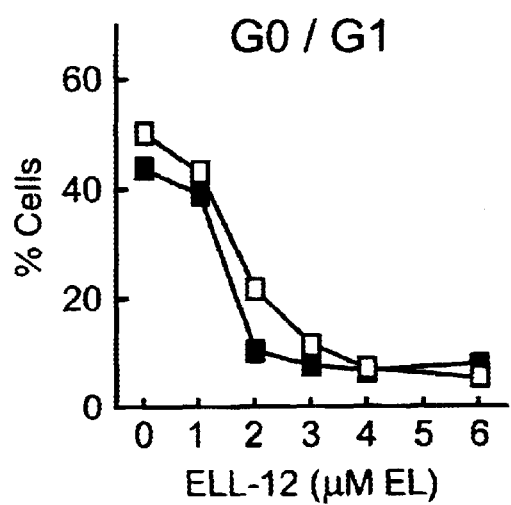
G0 / G1
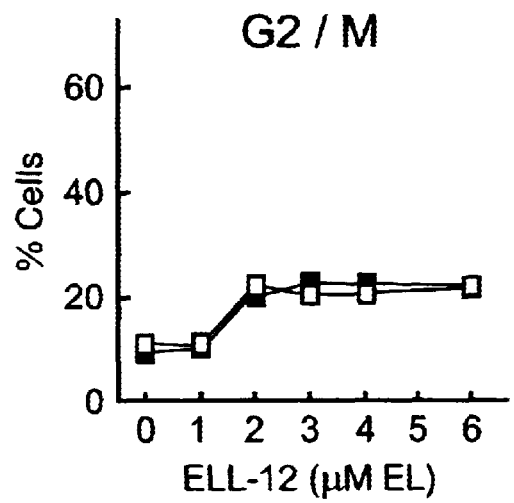
G2 / M
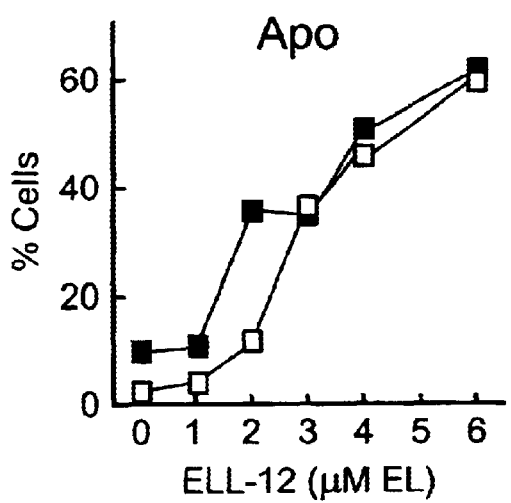
Apo
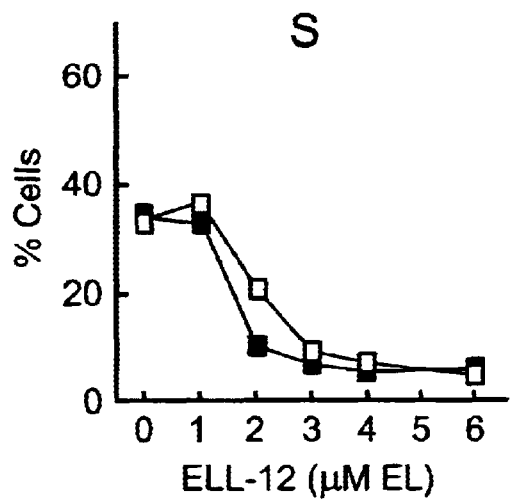
S
FIG. 5

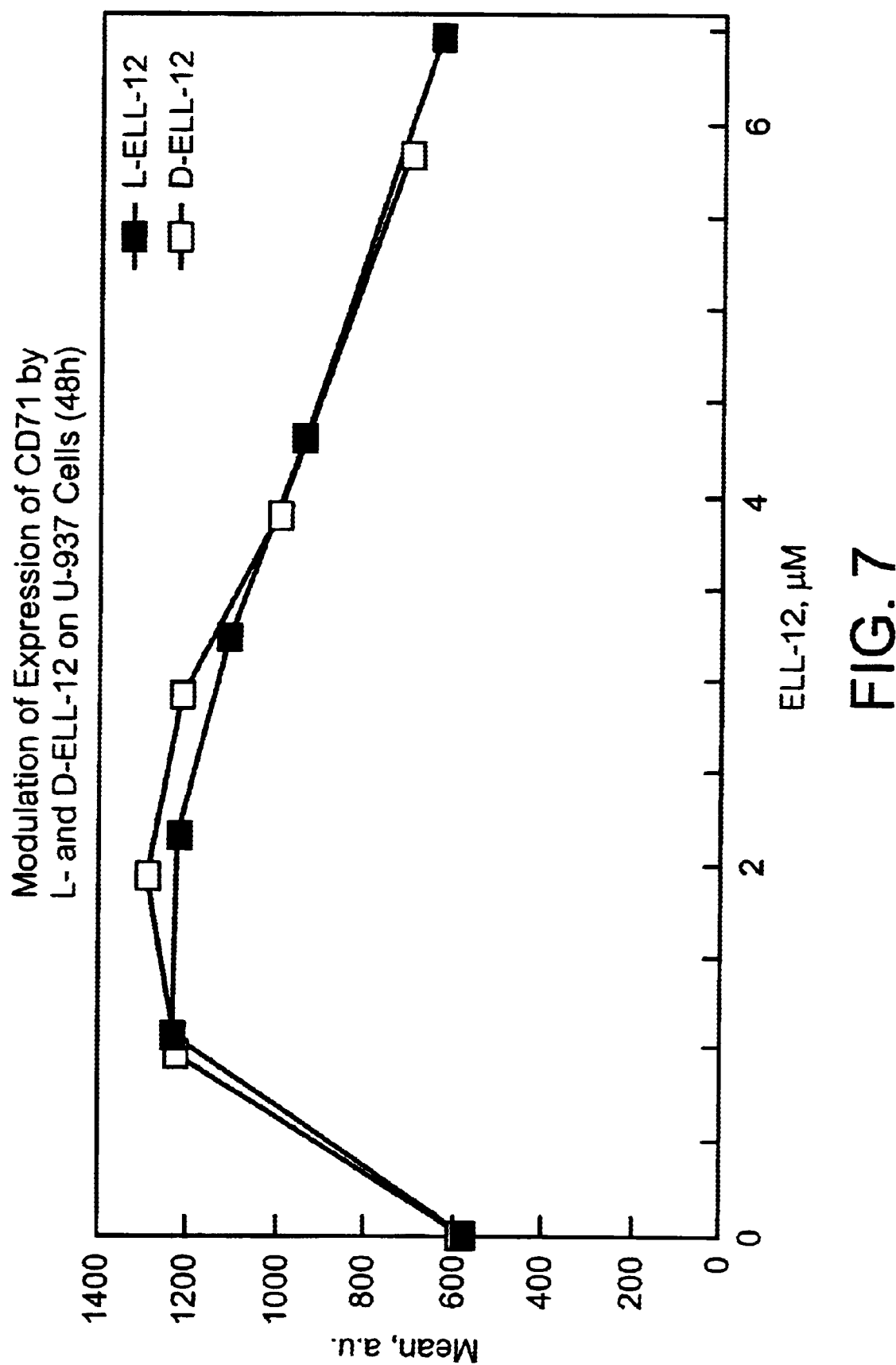

D AND L ETHERLIPID STEREOISOMERS AND LIPOSOMES

CROSS REFERENCE TO RELATED APPLICATIONS

This application is a continuation-in-part of U.S. application Ser. No. 09/390,395, filed Sep. 3, 1999, now U.S. Pat. No. 6,180,137, in turn a continuation of U.S. application Ser. No. 09/017,440, filed Feb. 2, 1998, now U.S. Pat. No. 5,965,159, in turn a continuation-in-part of U.S. application Ser. No. 08/602,669, filed Feb. 16, 1996, now U.S. Pat. No. 5,762,958.

FIELD OF THE INVENTION

The invention relates to a liposome comprising an ether lipid stereoisomer in the lipid bilayer of the liposome. The invention also encompasses pharmaceutical compositions comprising the liposome and methods of treating an animal with the liposome.

BACKGROUND OF THE INVENTION

Pharmaceutical therapeutics useful in the treatment of cancers or inflammatory conditions generally aim to slow the growth of, or destroy cancer cells or modulate the cells responsible for inflammatory responses. Optimal therapeutics, for instance cancer chemotherapy provides the decrease or eradication of cancer cell growth while avoiding or diminishing collateral damage to normal cells and tissues. The most effective anticancer agents are able to selectively target cancer cells while leaving normal cells relatively unaffected. Some etherlipids have been shown to be effective anticancer agents. However, the use of most etherlipids in vivo (to treat animals) has been accompanied by certain levels of toxicity to normal cells. Etherlipids are amphipathic lipids with ether linkages connecting their hydrocarbons with their molecular backbones. They are synthetic analogs of platelet activating factor ("PAF"; 1-O-2-acetyl-sn-glycero-3-phosphocholine). PAF is an effector believed to be involved in a variety of physiological processes, such as inflammation, immune responses and allergic reactions.

Ether lipids can accumulate in cell membranes, following which the lipids may affect the cells in a number of ways. Cell membrane accumulation can lead to disturbance of membrane lipid organization by a detergent-like activity of ether lipids; membrane structure, and hence, cell stability, can be disrupted by this activity. Phospholipid metabolism can also be disrupted, as the activities of several of the enzymes involved, e.g., CTP: phosphocholine cytidyl transferase, diacylglycerol kinase, sodium/potassium adenosine triphosphate phosphatase, acyl transferases, lysophospholipase, and phospholipases C and D, are inhibited in the presence of ether lipids. Ether lipids can also affect transmembrane signaling pathways, nutrient uptake, cellular differentiation and apoptosis.

Moreover, ether lipids are believed to be cytotoxic to cancer cells, and have been shown to be effective anticancer agents in animals (see, for example, Lohmeyer and Bittman, 1994; Lu et al. (1994a); Lu et al. (1994b); Dietzfelbinger et al. (1993); Zeisig et al. (1993); Berdel (1991); Workman (1991); Workman et al. (1991); Bazill and Dexter (1990); Berdel (1990); Guivisdalsky et al. (1990a); Guivisdalsky et al. (1990b); Powis et al. (1990); Layton et al. (1980); Great Britain Patent No. 1,583,661; U.S. Pat. No. 3,752,886). However, ether lipids are generally not toxic to most normal cells. Ether lipids' ability to act selectively on cancer cells is believed to be due to the cancer cells' lack of the alkyl cleavage enzymes necessary for hydrolysis of the lipids; the resulting intracellular lipid accumulation can disrupt the cell' functioning in a variety of ways. Normal cells typically possess these enzymes, and hence, are able to prevent the intracellular accumulation of ether lipids.

However, not all normal cells contain sufficient levels of alkyl cleavage enzymes to prevent intracellular ether lipid accumulation. Cells which do not possess the requisite levels of the enzymes can be subject to the same disruptive effects of ether lipid action as are cancer cells. Red blood cells, for example, lack the requisite alkyl cleavage enzymes, and hence, are also subject to a detergent-like activity of ether lipids. Hemolysis which results from exposure of these cells to ether lipids having detergent-like activity can be a major drawback to therapeutic use of the ether lipids (see, for example, Houlihan et al., 1995).

A number of different approaches are potentially available for decreasing or eliminating such drug-induced toxicity. One such approach is to incorporate the drugs into lipid-based carriers, e.g., liposomes. Such carriers can buffer drug toxicity, for example, by sequestering the drug in the carrier such that the drug is unavailable for inducing toxicity. Lipid carriers can also buffer drug-induced toxicity by interacting with the drug such that the drug is then itself unable to interact with the cellular targets through which it exerts its cytotoxic effects. The carriers also maintain the ability of the drugs to be therapeutically effective when released therefrom, e.g., when the carriers are broken down in the vicinity of tumors.

U.S. Pat. No. 5,762,958, incorporated herein by reference, describes a liposome having an ether lipid as a component of the liposome's lipid bilayer. Such liposomes reduce the toxicity of the ether lipids without inhibiting their anti-cancer efficacy. Nevertheless, there is no suggestion in U.S. Pat. No. 5,762,958 that the chirality of the ether lipid would have any effect on the toxicity of the liposomal formulation.

SUMMARY OF THE INVENTION

This invention provides a liposome having a lipid bilayer which comprises: an ether lipid having either a D or L chirality. Preferably, the lipid bilayer of the liposome comprises at least one lipid in addition to the D or L etherlipid. Most preferably, the liposome comprises (a) an underivatized phosphatidylcholine; (b) a sterol; (c) about 5–20 mole % of a phosphatidylethanolamine linked to a dicarboxylic acid at the ethanolamine group of the phosphatidylethanolamine (also referred to herein as the "headgroup-derivatized lipid"), and (d) greater than about 10 mole % to less than about 30 mole % of either the L or D stereoisomer of an ether lipid. Preferably, the ether lipid has the following formula:

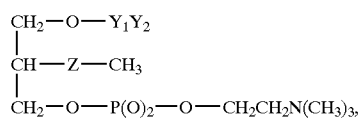

wherein $Y_1$ is $(CH_2)_{n1}(CH=CH)_{n2}(CH_2)_{n3}(CH=CH)_{n4}(CH_2)_{n5}(CH=CH)_{n6}(CH_2)_{n7}(CH=CH)_{n8}(CH_2)_{n9}$. The sum of $n1+2n2+n3+2n4+n5+2n6+n7+2n8+n9$ is an integer of from 3 to 23, n1 is zero or an integer of from 1 to 22, n3 is zero or an integer of from 1 to 19, n5 is zero or an integer of from 1 to 16, n7 is zero or an integer of from zero to 16, n9 is zero or an integer of from 1 to 10, and each of n2, n4, n6 and 8 is independently zero or 1. $Y_2$ is $CH_3$ or $CO_2H$.

Z is oxygen or sulfur. Preferably, Z is O; accordingly, this invention's glycerol-based etherlipids preferably have a methoxy group at the sn-2 position of their glycerol backbone.

Most preferably, the etherlipid is a D or L stereoisomer of the formula

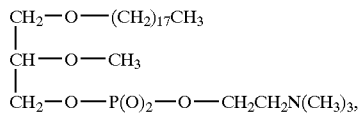

also known as "ET-18-OCH$_3$," or "edelfosine").

Preferably, the liposome is a unilamellar liposome having a diameter of from greater than about 50 nm to less than about 200 nm, the underivatized phosphatidylcholine is an unsaturated or partially unsaturated phosphatidylcholine, more preferably, dioleoyl phosphatidylcholine, and the sterol is cholesterol. The headgroup derivatized lipid preferably comprises a phosphatidylethanolamine ("PE") selected from the group consisting of dipalmitoyl phosphatidylethanolamine, palmitoyloleoyl phosphatidylethanolamine and dioleoyl phosphatidylethanolamine, and a dicarboxylic acid selected from the group consisting of glutaric acid, sebacic acid, succinic acid and tartaric acid. More preferably, the PE is dioleoyl phosphatidylethanolamine and the dicarboxylic acid is glutaric acid.

Preferred embodiments of this invention's liposome have bilayers containing dioleoyl phosphatidylcholine as the underivatized PC, cholesterol as the sterol, dioleoyl phosphatidylethanolamine-glutaric acid as the headgroup-derivatized lipid and ET-18-OCH$_3$ as the ether lipid. Most preferably, presently, the liposome's bilayer comprises about 20 mole percent of the ether lipid, about 10 mole percent of the headgroup-derivatized lipid, about 30 mole percent cholesterol and about 40 mole percent dioleoyl phosphatidylethanolamine. The liposome can further comprise an additional bioactive agent, that is an agent in addition to the ether lipid.

Also provided herein is a pharmaceutical composition comprising a pharmaceutically acceptable carrier and the liposomes of this invention. Further provided is a method of treating a mammal afflicted with a cancer, including, but not limited to: a lung, brain, colon, ovarian or breast cancer. The method comprises administering the compositions of this invention to the mammal, in an amount containing an anticancer effective amount of the ether lipid. Preferably, the liposome administered is a unilamellar liposome having an average diameter of from about 50 nm to about 200 nm. Typically, the anticancer effective amount of the etherlipid is from about 0.1 mg of the etherlipid per kg of the body weight of the mammal to about 1000 mg per kg.

The method can also comprise administration of an additional bioactive agent, e.g., an antineoplastic agent, antimicrobial agent, therapeutic lipid or hematopoietic cell growth stimulating agent, to the mammal. Administration of such an additional agent is typically of an effective amount of the additional agent in connection with an anticancer effective amount of the etherlipid. However, when the additional agent is an anticancer agent, either the additional agent, the etherlipid, or both can be administered in a "sub-anticancer effective amount," that is, in an amount which may not be effective against a cancer on its own.

Still further provided herein is a method of treating a mammal afflicted with an inflammatory disorder, e.g., an arthritic condition, asthmatic disorder or allergic reaction, which comprises administering this invention's pharmaceutical composition to the mammal, in an amount containing an anti-inflammation effective amount of the etherlipid. Typically, the anti-inflammation effective amount of the etherlipid is from about 0.1 mg of the etherlipid per kg of the body weight of the mammal to about 1000 mg per kg. Additional bioactive agents, such as additional anti-inflammatory agents, can also be administered when the liposomes of this invention are used against inflammatory disorders.

BRIEF DESCRIPTION OF THE DRAWINGS

FIG. 1 depicts the multi-step reaction for the stereospecific synthesis of L-ET-18-OCH$_3$ (L-edelfosine).

FIG. 5 depicts that L-EL and D-El induce similar changes in U-937 cell cycle (48 hours).

FIG. 7 depicts modulations of expression of CD71 by L- and D-ELL-12 on U-937 cells (48h).

DETAILED DESCRIPTION OF THE INVENTION

Figure 2:
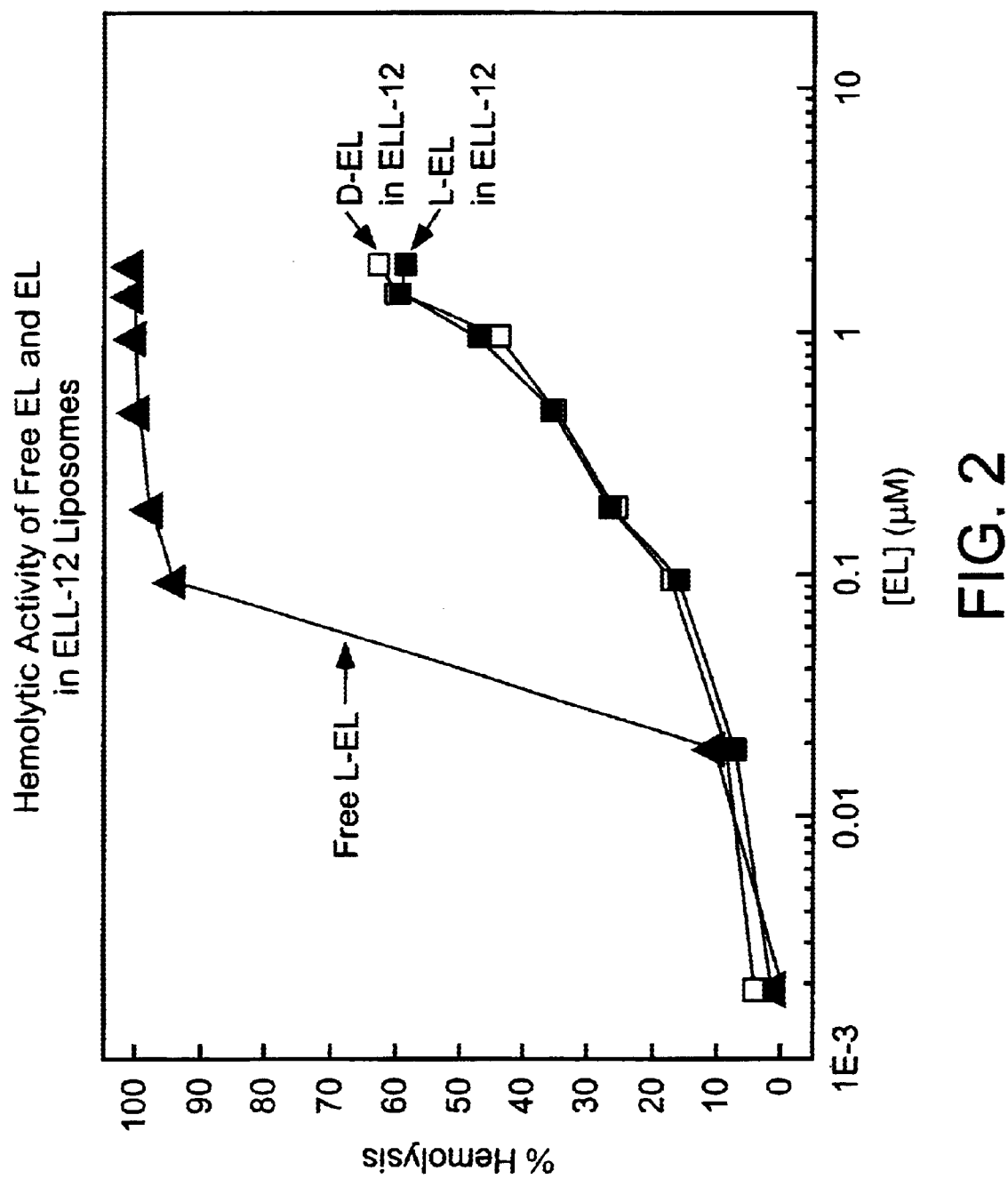
FIG. 2 depicts the results of the in vitro hemolysis assay.

Other than its critical stereoisomeric aspects, individual elements of the invention and their importance are described in detail in U.S. Pat. No. 5,762,958, incorporated herein by reference. The invention comprises a liposome having a D or L stereoisomer of an ether lipid as a component of the liposome's lipid bilayer. The liposomes comprising either or the two optical isomers or a racemic mixture of D and L etherlipids generally demonstrated equivalent in vitro growth inhibition against a variety of cell lines (A549, Lewis Lung, MCF7, MCF7/adr, L1210 and U-937). However, liposomes comprising the the D isomer optical isomer demonstrated a significantly significant greater activity against the L1210/vmdr line when compared to the L-isomer and the racemic mixture. However, in vivo, liposomes in accordance with the invention and comprising the L stereoisomer of the ether lipid component show superior anticancer efficacy by significantly reducing the mean number of tumor nodules of established B16/F10 lung tumors as compared to the same liposomes comprising the D ether lipid or the ether lipid racemate. Additionally, the L isomer formulation of liposomal etherlipid demonstrated significantly reduced toxicity compared to the D isomer liposome formulation when administered intraveneously once daily for 5 days. Both D and L isomers of the etherlipid and the racemic mxture exhibited similar hemolytic activity. This hemolytic activity was significantly attenuated by incorporation into liposomes according to the present invention.

Preferably, this invention comprises a liposome having a lipid bilayer which comprises: (a) an underivatized phosphatidylcholine; (b) a sterol; (c) a headgroup derivatized lipid containing a phosphatidylethanolamine and a moiety selected from the group consisting of dicarboxylic acids, gangliosides, polyethylene glycols and polyalkylethers, which headgroup-derivatized lipid comprises from about 5 mole percent to about 20 mole percent of the bilayer; and, (d) an etherlipid having the following formula:

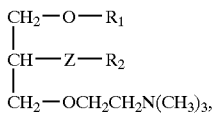

the etherlipid comprising from greater than about 10 mole percent, to less than about 30 mole percent, of the bilayer.

"Liposomes" are self-assembling structures comprising one or more lipid bilayers, each of which surrounds an aqueous compartment and comprises two opposing monolayers of amphipathic lipid molecules. Amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium.

Liposomes can have a single lipid bilayer (unilamellar liposomes, "ULVs"), or multiple lipid bilayers (multilamellar liposomes, "MLVs"), and can be made by a variety of methods (for a review, see, for example, Deamer and Uster (1983)). These methods include without limitation: Bangham's methods for making multilamellar liposomes (MLVs); Lenk's, Fountain's and Cullis' methods for making MLVs with substantially equal interlamellar solute distribution (see, for example, U.S. Pat. Nos. 4,522,803, 4,588,578, 5,030,453, 5,169,637 and 4,975,282); and Paphadjopoulos et al.'s reverse-phase evaporation method (U.S. Pat. No. 4,235,871) for preparing oligolamellar liposomes. ULVs can be produced from MLVs by such methods as sonication (see Paphadjopoulos et al. (1968)) or extrusion (U.S. Pat. No. 5,008,050 and U.S. Pat. No. 5,059,421). The etherlipid liposome of this invention can be produced by the methods of any of these disclosures, the contents of which are incorporated herein by reference.

Various methodologies, such as sonication, homogenization, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO89/008846), can also be used to regularize the size of liposomes, that is, to produce liposomes having a population of liposomes having less size heterogeneity, and a more homogeneous, defined size distribution. The contents of these documents are incorporated herein by reference. Liposome sizes can also be determined by a number of techniques, such as quasi-electric light scattering, and with equipment, e.g., Nicomp® particle sizers, well within the possession of ordinarily skilled artisans.

The liposomes of this invention can be unilamellar or multilamellar. Preferably the liposomes are unilamellar and have diameters of less than about 200 nm, more preferably, from greater than about 50 nm to less than about 200 nm. Smaller liposomes are generally believed to circulate longer in mammals, which are more quickly recognized by the mammals' reticuloendothelial systems ("RES"). Thus, 200 nm liposomes, for example, are generally expected to remain in circulation longer than liposomes having a 500-nm diameter. Longer circulation can enhance therapeutic efficacy by allowing more liposomes to reach their intended site of actions, e.g., tumors or inflammations. However, small liposomes, i.e., those generally less than 50 nm in diameter, carry amounts of bioactive agents which may be, in some cases, too low to be of sufficient therapeutic benefit.

$R_1$ of the etherlipid, the chain attached at the carbon #1 position of its glycerol backbone by way of an oxygen, has the formula $Y_1Y_2$, wherein $Y_2$ is $CH_3$ or $CO_2H$, but preferably is $CH_3$, and $Y_1$ is —$(CH_2)_{n1}(CH=CH)_{n2}(CH_2)_{n3}$ $(CH=CH)_{n4}(CH_2)_{n5}(CH=CH)_{n6}(CH_2)_{n7}(CH=CH)_{n8}$ $(CH_2)_{n9}$. n1 is equal to zero or is an integer of from 1 to 23; n3 is equal to zero or is an integer of from 1 to 20; n5 is equal to zero or is an integer of from 1 to 17; n7 is equal to zero or is an integer of from 1 to 14; n9 is equal to zero or is an integer of from 1 to 11; and each of n2, n4, n6 and 8 is independently equal to zero or 1. The sum of n1+2n2+n3+2n4+n5+2n6+n7+2n8+n9 is an integer of from 3 to 23; that is, the chain is from 4–24 carbon atoms in length.

The hydrocarbon chain is preferably saturated, that is, it preferably has no double bonds between adjacent carbon atoms, each of n2, n4, n6 and n8 then being equal to zero. Accordingly, $R_1$ is preferably $(CH_2)_{n1}CH_3$. More preferably, $R_1$ is $(CH_2)_{17}CH_3$. Alternatively, the chain can have one or more double bonds, that is, it can be unsaturated, and one or more of n2, n4, n6 and n8 can be equal to 1. For example, when the unsaturated hydrocarbon has one double bond, n2 is equal to 1, n4, n6 and n8 are each equal to zero and $Y_1$ is $(CH_2)_{n1}CH=CH(CH_2)_{n3}$. n1 is then equal to zero or is an integer of from 1 to 21, and n3 is also zero or is an integer of from 1 to 20, at least one of n1 or n3 not being equal to zero.

Z is oxygen, sulfur, NH, or —NHC(O)—, Z then being connected to the methyl group by way of either the nitrogen or carbonyl carbon. Z can also be —OC(O)—, it then being connected to the methyl group by way of either the oxygen or carbonyl carbon atom. Preferably, Z is O; accordingly, this invention's glycerol-based etherlipids preferably have a methoxy group at the sn-2 position of their glycerol backbone.

$R_2$ is an alkyl group, or a halogen-substituted alkyl group, having the formula $(C(X_1)_{n10}(X_2)_{n11})_{n12}CX_3X_4X_5$, wherein each of $X_1$, $X_2$, $X_3$, $X_4$, and $X_5$ is independently hydrogen or a halogen, but is preferably hydrogen. n10 is equal to zero, 1 or 2; n11 is equal to zero, 1, or 2; and n12 is equal to zero or an integer of from 1 to 23, but is most preferably, zero, $R_2$ then being $CX_3X_4X_5$. $X_3$, $X_4$, and $X_5$ are most preferably H, and $R_2$ then being $CH_3$. Accordingly, the etherlipid preferably has a methyl group attached to its carbon #2. However, $R_2$ can then also be $CH_2F$, $CHF_2$ or $CF_3$. When n12 is not zero, the sum of n10+n11 is equal to 2, n12 is preferably equal to 1, and $R_2$ is preferably $CH_2CH_3$, $CH_2CF_3$ or $CF_2CF_3$.

Preferably, the etherlipid is one in which $Y_2$ is $CH_3$, $R_1$ is $(CH_2)_{n1}CH_3$, R2 is $CH_3$ and Z is O. The preferred etherlipid is therefore:

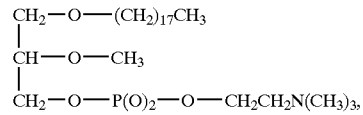

that is, 1-O-octadecyl-2-O-methyl-sn-glycero-3-phosphocholine ("ET-18-OCH$_3$" or "edelfosine").

Preferably, the underivatized PC is partially or wholly unsaturated, that is, it preferably has one or two acyl chains each having at least one double bond between adjacent carbon atoms in the chain. More preferably, presently, the underivatized PC is dioleoyl phosphatidylethanolamine ("DOPE").

"Sterols" generally affect the fluidity of lipid bilayers (see, for example, Lewis and McElhaney (1992) and Darnell et al. (1986)) Accordingly, sterol interactions with surrounding hydrocarbon chains generally inhibit emigration of these chains from the bilayer. The sterol component of the bilayers of the liposomes of this invention is preferably, but not necessarily, cholesterol, and can also be a variety of other sterolic compounds.

A "headgroup-derivatized" lipid is a lipid which, when present in a liposomal lipid bilayer with an etherlipid, can buffer the toxicity of the etherlipid. That is, the derivatized lipid can decrease the etherlipid's toxicity, such that it is generally less toxic than the free form of the etherlipid. Headgroup-derivatized lipids generally are amphipathic lipids comprising one or more hydrophobic acyl chains, and a phosphorylethanolamine group to which a suitable chemical moiety has been attached. The acyl chains typically contain from 4 to 24 carbon atoms, can be saturated or unsaturated and include palmitate and oleate chains, amongst others.

Preferred acyl chains are those which can adopt compatible packing configurations with the hydrophobic portions of other lipids present in the bilayer, and which can interact with an etherlipid such that release of the etherlipid from the bilayer is inhibited and etherlipid toxicity is buffered. More preferably, the headgroup derivatized lipid used herein is dipalmitoyl phosphatidylethanolamine ("DPPE"), palmitoyloleoyl phosphatidylethanolamine ("POPE") or dioleoyl phosphatidylethanolamine ("DOPE"). Most preferably, presently, the lipid is DOPE.

Chemical moieties suitable for attachment to such lipids are those, such as dicarboxylic acids, gangliosides, polyethylene glycols, polyakyl ethers and the like, which can be attached to a phosphorylethanolamine and which give rise to lipids having toxicity buffering, circulation-enhancing properties. Means of identifying suitable chemical moieties, for example by subjecting derivatized lipids to in vitro and in vivo toxicity testing, are well known to, and readily practiced by, ordinarily skilled artisans given the teachings of this invention. Means of attaching chemical moieties to polar groups are also well known to, and readily practiced by, ordinarily skilled artisans.

Toxicity buffering capacities of headgroup-derivatized lipids can be determined by a number of in vitro and in vivo testing methods well known to, and readily practiced by, ordinarily skilled artisans, given the teachings of this invention. For example, etherlipid-induced red blood cell (RBC) hemolysis can be examined in vitro by combining an etherlipid with a RBC suspension, incubating the combination, and then quantitating the percentage of RBC lysis by spectrophotometry.

A compound's therapeutic window "TW" is derived from the relationship between the compound's induction of hemolysis and its ability to inhibit the growth of tumor cells. TW values are determined in accordance with the formula $HI_5/GI_{50}$ (wherein "$HI_5$" equals the concentration of agent inducing the hemolysis of 5% of the red blood cells in a culture, and wherein "$GI_{50}$" equals the dose of an agent inducing fifty percent growth inhibition in a population of cells exposed to the agent). The higher an agent's $HI_5$ value, the less hemolytic is the agent; as $HI_5$'s increase, an agent is required to be present in greater concentration in order to induce 5% hemolysis than would be the case if the agent's $HI_5$ value was lower. Hence, the higher its $HI_5$, the more therapeutically benefical is an agent. By contrast, lower $GI_{50}$'s indicate better therapeutic agents—a lower $GI_{50}$ value indicates that a lesser concentration of an agent is required for 50% growth inhibition. Accordingly, the higher is an agent's TW, that is the higher is its $HI_5$ value and the lower is its $GI_{50}$ value, the better are the agent's therapeutic properties.

Generally, when a bioactive agent's TW is less than 1, the agent cannot be used effectively. That is, the agent's HI5 value is sufficiently low, and its GI50 value sufficiently high, that it is generally not possible to administer enough of the agent to achieve a sufficient level of tumor growth inhibition without also attaining an unacceptable level of hemolysis. Etherlipid liposomes having bilayers comprising headgroup-derivatized lipids can have TW's of greater than 1. Preferably, the TW of an etherlipid in a liposomal bilayer also comprising a headgroup-derivatized lipid is greater than about 1.5, more preferably, greater than about 2 and still more preferably, greater than about 3.

Headgroup-derivatized lipids can also be circulation-enhancing lipids, that is, the modifications directed to lipid toxicity buffering can also afford circulation enhancement. Accordingly, headgroup-derivatized lipids can inhibit clearance of liposomes from the circulatory systems of animals to which they have been administered. Liposomes are generally believed to be cleared from an animal's body by way of its reticuloendothelial system (RES). Avoiding RES clearance means that the frequency of liposome administration can be reduced, and that less of a liposome-associated bioactive agent need be administered to achieve desired serum levels of the agent. Enhanced circulation times can also allow targeting of liposomes to non-RES containing tissues.

Liposome outer surfaces are believed to become coated with serum proteins, such as opsonins, in animals' circulatory systems. Without intending in any way to be limited by theory, it is believed that liposome clearance can be inhibited by modifying the outer surface of liposomes such that binding of serum proteins thereto is generally inhibited. Effective surface modification, that is, alterations to the outer surfaces of liposomes which result in inhibition of opsonization and RES uptake, is believed to be accomplished by incorporating into liposomal bilayers lipids whose polar headgroups have been derivatized by attachment thereto of a chemical moiety which can inhibit the binding of serum proteins to liposomes such that the pharmacokinetic behavior of the liposomes in the circulatory systems of animals is altered (see, e.g., Blume et al. (1993); Gabizon et al. (1 993); Park et al. (1992); Woodle et al. U.S. Pat. No. 5,013,556; and, U.S. Pat. No. 4,837,028).

Presently, dicarboxylic acids, such as glutaric, sebacic, succinic and tartaric acids, are preferred components of headgroup-derivatized lipids. Most preferably, the dicarboxylic acid is glutaric acid ("GA"). Accordingly, suitable headgroup-derivatized lipids include phosphatidylethanolamine-dicarboxylic acids such as dipalmitoyl phosphatidylethanolamine-glutaric acid ("DPPE-GA"), palmitoyloleoyl phosphatidylethanolamine-glutaric acid ("POPE-GA") and dioleoyl phosphatidylethanolamine-glutaric acid ("DOPE-GA"). Most preferably, the derivatized lipid is DOPE-GA. The headgroup-derivatized can comprise from about 5 mole percent to about 50 mole percent of the liposome's lipid bilayer, but most preferably comprises about 10 mole percent of the bilayer.

The liposomes of this invention can comprise one or more additional lipids, that is, lipids in addition to the sterol, underivatized PE, headgroup-derivatized lipid and etherlipid already present in the liposomes' bilayers. Additional lipids are selected for their ability to adapt compatible packing conformations with the other lipid components of the bilayer such that the lipid constituents are tightly packed and release of the lipids from the bilayer is inhibited. Lipid-based factors contributing to compatible packing conformations are well known to ordinarily skilled artisans and include, without limitation, acyl chain length and degree of unsaturation, as well as the headgroup size and charge. Accordingly, suitable additional lipids, including various phosphatidylcholines ("PC's") such as egg phosphatidylcholine ("EPC") or dioleoyl phosphatidylcholine ("DOPC") can be selected by ordinarily skilled artisans without undue experimentation.

Preferred embodiments of this invention have the underivatized PE being DOPE, the sterol being cholesterol ("chol"), the etherlipid being ET-18-OCH3 and the headgroup-derivatized lipid being DOPE-GA. Most preferably, presently, the liposome comprises DOPE, chol, ET-18-O—$CH_3$ in a respective molar ratio of 4:3:1:2, wherein DOPE comprises 40 mole % of the liposomes' bilayers, chol 30% mole, DOPE-GA 10 mole % and the etherlipid 20 mole %. Preferably, the liposomes are unilamellar and have an average diameter of from about 50 nm to about 200 nm, "average" meaning that the median diameter of a population of this invention's liposomes is between 50 and 200 mn.

The liposome can comprise an additional bioactive agent, that is, a bioactive agent in addition to the etherlipid. A "bioactive agent" is any compound or composition of matter that can be administered to animals, preferably humans. Such agents can have biological activity in animals; the agents can also be used diagnostically in the animals.

Bioactive agents which may be associated with liposomes include, but are not limited to: antiviral agents such as acyclovir, zidovudine and the interferons; antibacterial agents such as aminoglycosides, cephalosporins and tetracyclines; antifungal agents such as polyene antibiotics, imidazoles and triazoles; antimetabolic agents such as folic acid, and purine and pyrimidine analogs; antineoplastic agents such as the anthracycline antibiotics and plant alkaloids; sterols such as cholesterol; carbohydrates, e.g., sugars and starches; amino acids, peptides, proteins such as cell receptor proteins, immunoglobulins, enzymes, hormones, neurotransmitters and glycoproteins; dyes; radiolabels such as radioisotopes and radioisotope-labelled compounds; radiopaque compounds; fluorescent compounds; mydriatic compounds; bronchodilators; local anesthetics; and the like.

Liposomal bioactive agent formulations can enhance the therapeutic index of the bioactive agent, for example by buffering the agent's toxicity. Liposomes can also reduce the rate at which a bioactive agent is cleared from the circulation of animals. Accordingly, liposomal formulation of bioactive agents can mean that less of the agent need be administered to achieve the desired effect. Additional bioactive agents preferred for the liposome of this invention include antimicrobial, anti-inflammatory and antineoplastic agents, or therapeutic lipids, for example, ceramides. Most preferably, the additional bioactive agent is an antineoplastic agent.

Liposomes can be loaded with one or more biologically active agents by solubilizing the agent in the lipid or aqueous phase used to prepare the liposomes. Alternatively, ionizable bioactive agents can be loaded into liposomes by first forming the liposomes, establishing an electrochemical potential, e.g., by way of a pH gradient, across the outermost liposomal bilayer, and then adding the ionizable agent to the aqueous medium external to the liposome (see Bally et al. U.S. Pat. No. 5,077,056 and WO86/01102).

The liposome of this invention can be dehydrated, stored and then reconstituted such that a substantial portion of its internal contents are retained. Liposomal dehydration generally requires use of a hydrophilic drying protectant such as a disaccharide sugar at both the inside and outside surfaces of the liposome bilayers (see U.S. Pat. No. 4,880,635). This hydrophilic compound is generally believed to prevent the rearrangement of the lipids in the liposome, so that the size and contents are maintained during the drying procedure and through subsequent rehydration. Appropriate qualities for such drying protectants are that they be strong hydrogen bond acceptors, and possess stereochemical features that preserve the intramolecular spacing of the liposome bilayer components. Alternatively, the drying protectant can be omitted if the liposome preparation is not frozen prior to dehydration, and sufficient water remains in the preparation subsequent to dehydration.

Also provided herein is a pharmaceutical composition comprising a pharmaceutically acceptable carrier and the liposome of this invention. "Pharmaceutically acceptable carriers" as used herein are those media generally acceptable for use in connection with the administration of lipids and liposomes, including liposomal bioactive agent formulations, to animals, including humans. Pharmaceutically acceptable carriers are generally formulated according to a number of factors well within the purview of the ordinarily skilled artisan to determine and account for, including without limitation: the particular liposomal bioactive agent used, its concentration, stability and intended bioavailability; the disease, disorder or condition being treated with the liposomal composition; the subject, its age, size and general condition; and the composition's intended route of administration, e.g., nasal, oral, ophthalmic, topical, transdermal, vaginal, subcutaneous, intramammary, intraperitoneal, intravenous, or intramuscular (see, for example, Nairn (1985)). Typical pharmaceutically acceptable carriers used in parenteral bioactive agent administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

Further provided is a method of treating a mammal afflicted with a cancer, e.g., a brain, breast, lung, colon or ovarian cancer, or a leukemia, lymphoma, sarcoma, carcinoma, which comprises administering the pharmaceutical composition of this invention to the mammal, etherlipids being believed to be selectively cytotoxic to tumor cells. Generally, liposomal etherlipids can be used to treat cancers treated with free, that is, nonliposomal, etherlipids. However, encapsulation of an etherlipid in a liposome can enhance its therapeutic index, and therefore make the liposomal etherlipid a more effective treatment.

An amount of the composition comprising an anticancer effective amount of the etherlipid, typically from about 0.1 to about 1000 mg of the lipid per kg of the mammal's body, is administered, preferably intravenously. For the purposes of this invention, "anticancer effective amounts" of liposomal etherlipids are amounts effective to inhibit, ameliorate, lessen or prevent establishment, growth, metastasis or invasion of one or more cancers in animals to which the etherlipids have been administered. Anticancer effective amounts are generally chosen in accordance with a number of factors, e.g., the age, size and general condition of the subject, the cancer being treated and the intended route of administration, and determined by a variety of means, for example, dose ranging trials, well known to, and readily practiced by, ordinarily skilled artisans given the teachings of this invention. Antineoplastic effective amounts of the liposomal etherlipid of this invention are about the same as such amounts of free, nonliposomal, etherlipids.

Preferably, the liposome administered is a unilamellar liposome having an average diameter of from about 50 nm to about 200 nm. The anti-cancer treatment method can include administration of one or more bioactive agents in addition to the liposomal etherlipid, these additional agents preferably, but not necessarily, being included in the same liposome as the etherlipid. The additional bioactive agents, which can be entrapped in liposomes' internal compartments or sequestered in their lipid bilayers, are preferably, but not necessarily, anticancer agents or cellular growth promoting factors.

This invention also provides a method of treating a mammal afflicted with an anti-inflammatory disorder, e.g., arthritic conditions, asthmatic disorders and allergic reactions, comprising administering to the mammal an amount of the pharmaceutical composition provided herein sufficient to contain an anti-inflammation effective amount of the liposomal etherlipid. Inflammation is a process of cytological and histological reactions occurring in affected blood vessels, and surrounding tissues, in response to an injury (see, e.g., *Stedman's Medical Dictionary (Illustrated)* (1982)). Inflammatory responses to such stimuli include local reactions and resulting morphological changes, destruction or removal of injurious materials and activation of repair mechanisms. Thus, inflammation can be part of the process by which animals heal themselves.

However, inflammation can also occur in response to abnormal physiological stimuli, and can cause problems in the body. Joints, for example, become inflamed in arthritic conditions such as gout, filary arthritis, rheumatoid arthritis and Lyme disease (see, e.g., *Stedman's Medical Dictionary (Illustrated)*, supra at pages 123–124). These states may be characterized by the extravasation of cells, i.e, the egress of cells from the circulation into the inflamed area. Agents which can inhibit such extravasation, or which can otherwise inhibit inflammatory responses to abnormal physiological stimuli, can be used to ameliorate the inflammation. An "anti-inflammation effective amount" of a liposomal etherlipid, typically from about 0.1 mg to about 1000 mg per kg of a treated mammal's body weight, is any amount of the etherlipid effective to ameliorate, inhibit or prevent inflammatory responses or reactions in animals afflicted with conditions characterized by abnormal inflammation, i.e., inflammation which is in response to abnormal physiological stimuli and which is not part of the body's normal repair processes in response to an injury.

This invention will be better understood from the following examples. However, those of ordinary skill in the art will readily understand that these examples are merely illustrative of the invention as defined in the claims which follow thereafter.

D and L etherlipid stereoisomers can be prepared in small quantities by techniques well known to those of ordinary skill in the art. These methods have been utilized to prepare L etherlipid. However, sufficient quantities of the D etherlipid of sufficient purity for in vitro and in vivo experiments were not commercially available. Non-limiting exemplary techniques are described in Examples 1 and 2.

EXAMPLE 1

Stereospecific Synthesis of L-ET18OCH$_3$ (L-edelfosine)

The synthesis of the L optical isomer of ET18OCH$_3$ (L-edelfosine) is a multi-step process. First, n-Octadecylalcohol is reacted with Mesylchloride to form n-Octadecylmesylate. After the reaction is complete, the mother liquor is concentrated until a solid residue is obtained. This residue is the first intermediate and is purified by crystallization and washed.

The next step involves reacting the n-Octadecylmesylate with 2,3-Isopropylidene-sn-glycerol, followed by hydrolysis to give 1-O-Octadecyl-sn-glycerol. The 1-O-Octadecyl-sn-glycerol is purified by crystallization, washed and dried.

Next, the 1-O-Octadecyl-sn-glycerol is reacted with triphenylmethylchloride (tritylchloride). The reaction mixture in this step is worked up and concentrated. The 1-O-Octadecyl-3-O-trityl-sn-glycerol product is crystallized and washed.

The 1-O-Octadecyl-3-O-trityl-sn-glycerol is reacted with Methyliodide to form a 1-O-Octadecyl-2-O-methyl-3-O-trityl-sn-glycerol product. After crystallyzation of the product, the trityl group is hydrolyzed to give 1-O-Octadecyl-2-O-methyl-sn-glycerol, which is subsequently purified by chromatography and crystallization.

The 1-O-Octadecyl-2-O-methyl-sn-glycerol prepared above is reacted with Phosphorus oxychloride and then with Choline tosylate to form the crude Ether Lipid. The reaction mixture is worked up and concentrated under vacuum. The crude Ether Lipid is obtained by crystallization, centrifugation and washing.

This multi-step reaction is summarized on FIG. 1.

EXAMPLE 2

Stereospecific Synthesis of D-ET18OCH$_3$ (D-edelfosine)

In the first step of the multi-step synthesis of the D optical isomer of ET18OCH$_3$ (D-edelfosine), n-Octadecylalcohol is reacted with Mesylchloride to form n-Octadecylmesylate. The mother liquor is concentrated until a solid residue is obtained. This residue is purified by crystallization and washed.

The second step involves reacting the n-Octadecylmesylate with 1,2-Isopropylidene-sn-glycerol, followed by hydrolysis to give 1-O-Octadecyl-sn-glycerol. The 1-O-Octadecyl-sn-glycerol is purified by crystallization, washed and dried.

The third step involves reacting 1-O-Octadecyl-sn-glycerol with triphenylmethylchloride (tritylchloride). The reaction mixture in this step is worked up and concentrated. The 1-O-Octadecyl-3-O-trityl-sn-glycerol product is crystallized and washed.

The fourth step involves reacting the 1-O-Octadecyl-3-O-trityl-sn-glycerol with Methyliodide to form a 1-O-Octadecyl-2-O-methyl-3-O-trityl-sn-glycerol product. After crystallyzation of the product, the trityl group is hydrolyzed to give 1-O-Octadecyl-2-O-methyl-sn-glycerol, which is subsequently purified by chromatography and crystallization.

The fifth step involves reacting 1-O-Octadecyl-2-O-methyl-sn-glycerol with Phosphorus oxychloride and then with Choline tosylate to form the crude Ether Lipid. The reaction mixture is worked up and concentrated under vacuum. The crude Ether Lipid is obtained by crystallization, centrifugation and washing.

Liposomal formulations in accordance with the invention were prepared and evaluated as described in the following examples.

EXAMPLE 3

Platelet Aggregation Assay

Liposomal formulations were prepared as described in U.S. Pat. No. 5,762,958, incorporated herein by reference.

The platelet aggregation effect of the liposomes in the whole blood of various mammals was evaluated using a CHRONO-LOG Dual Chamber Whole Blood Aggregometer Model 560, according to the following protocol:

Venous blood was collected using 3.8% sodium citrate in a Vacutainer. Dilution ratio is 1 to 9 (citrate solution: blood). The effect of D and L etherlipid and liiposmes containing them on aggregation of platelets from rats, dogs, monkeys and humans was tested.

Immediately following collection the blood was mix by gentle inversion (maintain at room temperature). Prewarm 500 ul saline in disposable plastic cuvettes. Add 500 ul whole blood or PRP. Add disposable siliconized mini stir bar. Warm diluted blood 5 min at 37° C. prior to testing. Add test samples to aggregation chambers and insert impedance probes.

Platelet aggregation response was determined by increased resistance using an impedance electrode in a platelet suspension. Resistance measurements were taken 6-8 minutes after addition of the test article to 1 ml whole blood or platelet rich plasma (PRP). The results of the evaluations are reported in Table 1.

TABLE 1

Platelet Aggregation Response in Whole Blood

| Treatment | Concentration | Dog Blood Response ($\Omega$) | Rat Blood Response ($\Omega$) | Human Blood Response ($\Omega$) |
|---|---|---|---|---|
| L-ELL | 100 $\mu M$ | 8.5 | 0 | 0 |
| D-ELL | 100 $\mu M$ | 0 | 0 | 0 |
| PAF | 0.05 $\mu M$ | 14.8 | 0 | 6.0 |
| ADP | 20 $\mu M$ | 4.0 | 2.0 | 6.3 |
| collagen | 20 $\mu g/\mu L$ | 12 | 34.1 | 36 |

The results reported in Table 1 show that while there was no platelet aggregation response in the whole rat and human blood from either the D or L ether lipid, there was a stereospecific response to the L-ether lipid in whole dog blood (the reactions to PAF, ADP and collagen to demonstrate the acceptability of each platelet preparation for testing).

EXAMPLE 4

To further investigate the platelet aggregation response triggered by the L-ether lipid in dog whole blood, the effect of a compound (CV-6209) that binds PAF binding sites on dog blood platelets was studied. The results are reported in Table 2.

TABLE 2

Platelet Aggregation Response in Dog Whole Blood

| Treatment | Concentration ($\mu M$) | Dog Blood Response ($\Omega$) |
|---|---|---|
| PAF | 0.05 | 23.5 |
| CV-6209/PAF | 0.25/0.05 | 0 |
| CV-6209/PAF | 0.10/0.05 | 18.5 |
| L-ether lipid | 100 | 18 |
| CV-6209/L-ether lipid | 0.25/100 | 0 |
| CV-6209/L-ether lipid | 0.10/0.05 | 12.5 |

The similar effects of the CV-6209 blinding molecule on the platelet aggregation response induced by PAF and L-etherlipid suggest that the molecules utilize the same binding sites on the dog blood platelets, and that the mechanisms by which molecules induce platelet aggregation are similar. Confirming the results in Example 3, the data in Table 2 indicates that dog blood platelets cannot distinguish between PAF and L-ether lipid.

EXAMPLE 5

Two liposomal formulations differing only in the chirality of ether lipid component were prepared, and their toxicity on C57/BL6 mice (3–10 per group) was studied. Groups of female C57/BL6 mice weighing 16–20 g were injected i.v. with various doses of ELL-12 (L or D) diluted in PBS. Single dose i.v. toxicity, using doses of 150 or 200 mg/kg of L or D ELL-12 was evaluated to determine the maximally tolerated dose (MTD=dose lethal in less than or equal to 10% of the test mice). The multiple dose MTD was determined by administering 50–150 mg/kg L or D ELL-12 i.v. once per day for 5 consecutive days. The mice were weighed and observed twice weekly and mortality was recorded daily. Experiments were terminated 30 days after the treatment. The results are reported in Tables 3. L and D isomers of ET-18-OCH3 formulated in ELL-12 differed in vivo when adminsitered intraveneously. L-ELL-12 exhibited less acute toxicity than D-ELL-12 when administered i.V.

TABLE 3

Toxicity of Stereoisomeric Ether Lipid Liposomal Formulations on C57/BL6 Mice

| Dose | Number of Survivors/ Total Mice per Group | |
|---|---|---|
| mg/kg | ELL-12(L) | ELL-12(D) |
| i.v. × 1 | | |
| 150 | 3/3 | 3/3 |
| 200 | 1/3 | 0/3 |
| i.v. × 5 daily | | |
| 50 | 5/5 | 5/5 |
| 75 | 5/5 | 0/5 |
| 100 | 1/5 | 0/5 |

EXAMPLE 6

The relative activity and toxicity of the two optical isomers of 1-O-octadecyl-2-O-methyl-sn-glycero-3-phosphocholine (EL; optical isomers L-EL and D-EL shown in Formulas I and II below) was investigated in this study. Accordingly, this study was designed to evaluate the activity of each optical isomer of EL, and the racemic mixture using a standardized in vitro growth inhibition assay with a diverse tumor cell line panel including cell lines expressing multiple drug resistance. Hemolysis of washed rat red blood cells in vitro was used as an assay of the potential toxicity of the test compounds.

Formula I: L-EL (1-O-octadecyl-2-O-methyl-sn-glycero-3-phosphocholine)

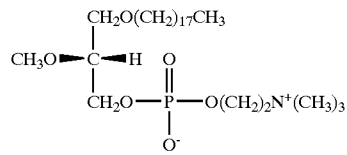

Formula II: D-EL (3-O-octadecyl-2-O-methyl-sn-glycero-1-phosphocholine)

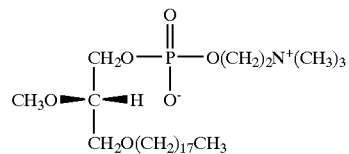

The anti-tumor activities of the D and L etherlipid were evaluated against A549, a human non-small cell lung carcinoma cell line; MCF 7, a human breast carcinoma line and MCF 7/adr, multi-drug resistant human breast carcinoma; were obtained from the DCT Tumor Repository (NCI-Frederick Cancer Research Facility, Frederick, Md.). U-937, a human histiocytic lymphoma cell line, was obtained from the American Type Culture Collection. Stock cultures of these human cell lines were maintained in RPMI 1640 tissue culture media (Life Technologies, Gaithersburg, Md.) supplemented with 10% heat inactivated fetal bovine serum (Life Technologies) and 10 mM HEPES (Life Technologies). Cultures were maintained in exponential growth in a humidified incubator with 5% CO2 and were passaged twice weekly. L1210 and L1210/vmdr, murine lymphocytic leukemias, (Yale University School of Medicine). L1210/vmdr, a selected line of L1210, was transfected with a plasmid (pHaMDR1/A) containing the mdr 1 gene.

A Sulforhodamine B (SRB) assay was employed to determine relative in vitro drug sensitivity using the $GI_{50}$ parameter (the concentration of drug which inhibits cell growth 50%). The detailed methodology of the SRB assay is described elsewhere (2,3). Briefly, 96-well microtiter plates were inoculated with 100 ul of the above cell lines at optimal cell densities, 3500–15,000 cells/well, in medium (RPMI 1640 with L-glutamine (Mediatech, Herndon, Va.)) supplemented with 10% fetal bovine serum (Life Technologies) for all cell lines. The plates were then incubated for 24 hours at 37° C., 100% humidity, and 5% $CO_2$. After the 24 hour incubation, 100 μl of medium was added to the designated time zero plates, then the plates containing adherent cell lines were acid fixed with 50 ul of 50% trichloroacetic acid (wt/vol) (Sigma, St. Louis, Mo.) and refrigerated at 4° C. for 1 hour (the suspension cell lines were acid fixed with 80% trichloroacetic acid). The supernatant was discarded and the plates were rinsed 6 times with water and air dried. Then the test compound was added (100 ul aliquots) to the remaining (non-fixed) plates at 2 times the predetermined highest concentration and serially diluted across the plates. Growth control wells received an additional 100 ul of medium. There were triplicate wells on each plate and duplicate plates (6 representative wells) for each drug concentration. The cells were then incubated for 72 hours under the above conditions. The treated plates were acid fixed, rinsed and dried as above. One hundred microliters of 0.4% SRB (Sigma) in 1% acetic acid (Sigma) was added to the plates and incubated at room temperature for 10 minutes. Unbound stain was removed by rinsing the plates 3 times with 1% acetic acid. The plates were air dried for 24 hours. The bound stain was solubilized with 100 ul of 10 mM Tris buffer (Sigma) and the optical density was read spectrophotometrically at 490 nm (Microplate Reader Model 3550-UV, Biorad, Hercules, Calif.). The raw optical density data was imported into an Excel (Microsoft, Redmond, W.Va.) spreadsheet to determine dose responses. Percent growth was calculated as follows: $(T-T_0)/(C-T_0) \times 100$ where (T)=mean optical density of treated wells at a given drug concentration, $(T_0)$=mean optical density of time zero wells, and (C)=mean optical density of control wells, or if $T<T_0$ where cell killing has occurred, then percent cell death can be calculated as follows: $(T-T_0)/(T_0) \times 100$. By varying drug concentration, dose response curves were generated and the $GI_{50}$ values were calculated. The $GI_{50}$ values for each experiment were calculated using data obtained from three duplicate wells on two separate plates. The mean $GI_{50}$ values and standard deviations were then calculated from the $GI_{50}$'s from each independent experiment.

An in vitro hemolysis assay for the test compound was also performed. Fresh whole blood was collected from anesthetized ($CO_2$) Sprague Dawley rats into EDTA monovets. A 4% RBC solution was prepared by centrifuging the blood at 1000 rpm to remove plasma and washing with Dulbecco's PBS (without $Ca^{++}$ and $Mg^{++}$). Each compound tested was dissolved/dispersed in PBS to 2×the final desired concentration. Equal volumes of the drug and RBC solution were mixed in glass test tubes, parafilmed, and placed in a 37° C. shaking incubator for 20 hours at a speed of 140 rpm. All samples were run in duplicate. After incubation, the samples were centrifuged to remove any remaining intact RBC's. The supernatants were transferred to clean test tubes and measured for absorbance at 550 nm against a distilled water blank. The percent hemolysis was calculated by the following equation:

$$\frac{\text{absorbance of supernatant (550 nm)}}{\text{absorbance of sample completelylysed}} \times 100$$

The complete hemolysis control was accomplished by repeated freeze-thaw cycles until the resulting pellet was absent or white. To better compare the hemolytic capabilities of the drugs, all drug concentrations were converted to uM. To account for interday variability of the 4% RBC solution, results were normalized to 0.4 OD. Where applicable, HI50 concentrations were calculated using WinNonlin version 1.1 Model 106 (sigmoid Emax)

The results of the in vitro growth inhibition study (SRB assay) are reported in Table 4, while the results of the in vitro hemolysis assay are graphically depicted in FIG. 2. Table 4 shows that the two optical isomers and the racemic mixture had generally equivalent activity against all cell lines ($GI_{50}$'s ranging from about 1.5 to 29 μM for the different cell lines) with the exception of the L1210/vmdr line in which D-EL showed a slight but statistically significant greater activity compared to L-EL and the racemate. Both isomers and racemic mixture were equally hemolytic to washed rat red blood cells in vitro with $H_{50}$'s ranging from 15.06 to 16.19 μM.

TABLE 4

In vitro growth inhibition after 72 hrs treatment GI$_{50}$ ($\mu$M ± sd)

| Compound | A549 | Lewis Lung | MCF7 | MCF7/adr | L1210 | L1210/vmdr | U937 |
|---|---|---|---|---|---|---|---|
| L-EL | 9.07 ± 0.39 | 29.13 ± 2.05 | 18.57 ± 4.57 | 27.95 ± 2.10 | 4.77 ± 0.41 | 8.77 ± 1.47 | 1.53 ± 0.42 |
| D-EL | 7.96 ± 0.57 | 25.45 ± 0.95 | 14.60 ± 5.92 | 25.12 ± 1.69 | 3.60 ± 1.59 | 4.87 ± 0.77[b] | 1.41 ± 0.29 |
| rac-EL | 8.36 ± 0.67 | 27.05 ± 1.98 | 15.86 ± 6.41 | 27.83 ± 0.30 | 4.18 ± 1.38 | 6.09 ± 2.15 | 1.50 ± 0.22 |

EXAMPLE 8

Figure 3:
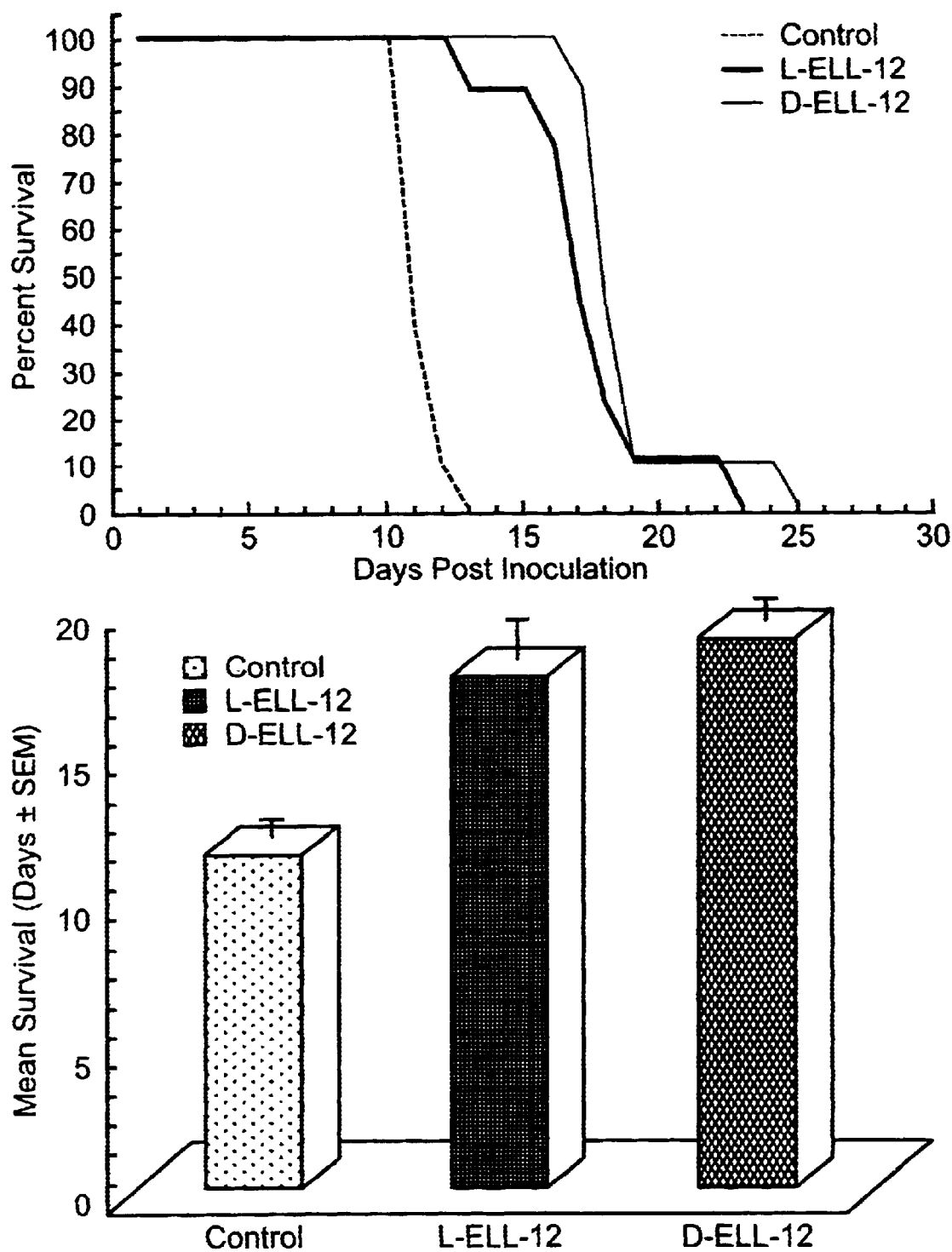
FIG. 3 depicts that D and L-ELL-12 administered i.p. were equally effective against P388leukemia

P388 Murine Leukemia. Female CDF1 mice (18–20 g) were injected i.p. with 1×10$^5$ P388 cells in 0.5 ml PBS on day 0. Mice were randomly divided into groups (n=10) and treated i.p. with control or 50 mg/kg ELL-12 (L or D) on days 1–10 post inoculation. Mortality was observed daily and mean survival time (MST) was calculated. FIG. 3 demonstrates that D and L ELL-12 administered i.p. were equally effective against P388 leukemia.

B16/F10 Murine Melanoma. In three separate experiments, female C57/BL6 (16–20 g) mice were injected i.v. with 5×10$^4$ B16/F10 cells on day 0. Mice were randomly divided into treatment groups (n=10) and treated i.v. with 6.25–12.5 mg/kg ELL-12 (L1 or D) or control on days 10, 12 14, 16, & 18 post inoculation. Mice were sacrificed on days 21 or 25 post inoculation, lungs were removed, fixed in 10% formalin, and tumor nodules counted in a blind fashion using a magnifier.

Figure 4:
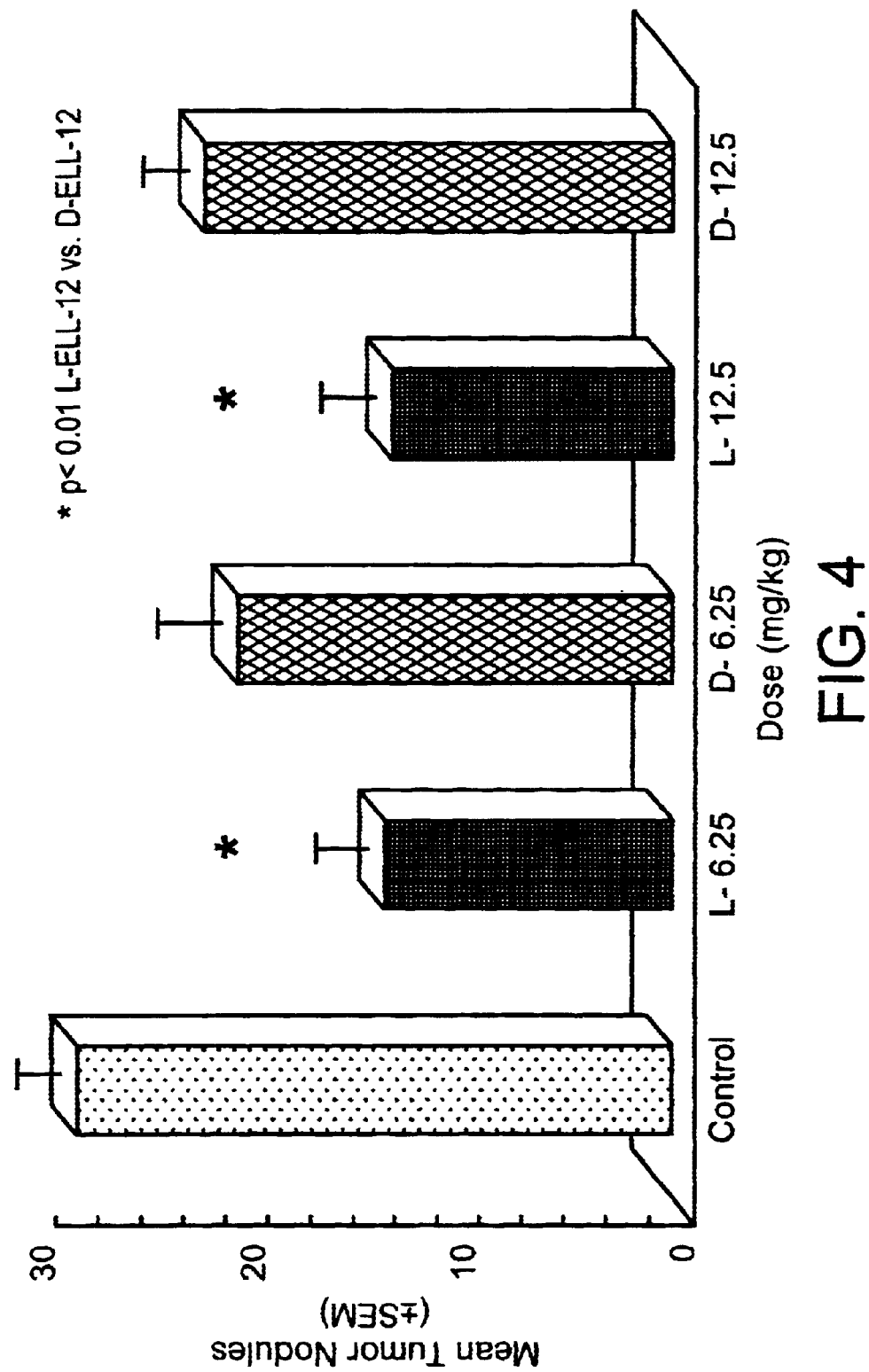
FIG. 4 depicts that the L isomer liposome formulation, when administered against established B16/F10 lung tumors significantly ($p<0.05$) reduced the mean number of tumor nodules when compared to control or the D isomer liposome formulation.

Due to module encroachment, the precise number of nodules was difficult to determine when counts were 30 or more per lung. The mean number of nodules per treatment group within each experiment was calculated. When the tumor nodule count was more than 30 nodules per lung, it was recorded as "30" for the calculation. Student's t-test was used to compare ELL-12 (L) vs. (D). FIG. 4 demonstrates that the L isomer liposome formulation, when administered against established B16/F10 lung tumors, significantly (p<0.05) reduced the mean number of tumor nodules when compared to control or the D isomer liposome formulation.

Hemolytic Activity. Hemolysis was assessed using washed red blood cells from Fisher rats that were adjusted to a cell density of 1×10$^8$ cells/ml. Samples were incubated at 37° C. for 30 minutes and certrifuged to pellet cells. Absorbances for the supernatants were measured at 550 nm and the results were expressed as percent hemolysis elicited by 1 mg/ml of ether lipid standard.

Cell Cycle Studies. Fixation and staining were performed as previously described (Exp. Cell Res. 207: 142–151). Briefly, 2×10$^6$ cells were collected and pelleted by centrifugation (1000 rpm, 4° C., 5 min). The cells were resuspended in 1 ml cold PBS (1×) and fixed by adding 4 ml of chilled absolute EtOH (−20° C.). Cells were stored at −20° C. To stain, the fixed cells were pelleted (1000 rpm, 5min) and resuspended in 1 ml PBS. One hundred $\mu$l of a 200 $\mu$g/ml RNAase (DNAase free), boiled 5–10 minutes before use, was added and the mixture incubated at 37° C. for 30 minutes. Propidium iodide (100 $\mu$l of a 1 mg/ml stock) was added and the samples were transferred to 12×75 Falcon tubes and read after 5–10 minutes. FIG. 5.

Figure 6:
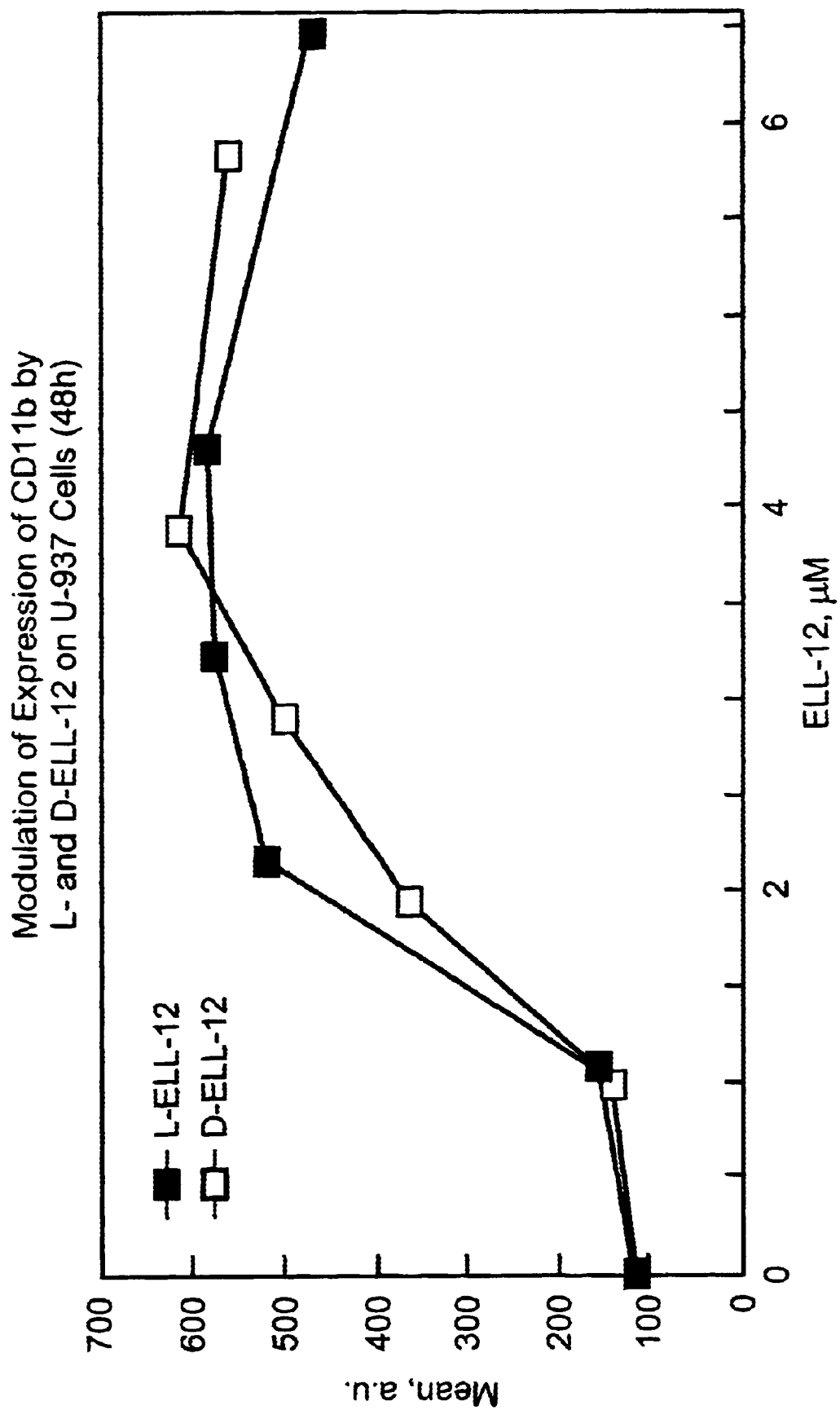
FIG. 6 depicts modulations of expression of CD11b by L- and D-ELL-12 on U-937 cells (48h).

Analysis of CD Expression. Monoclonal CD11b-PE was purchased from Ancell (Bayport, Minn.) and CD71-FITC and CD82-PE were purchased from Pharmingen (San Diego, Calif.). Monclonal IgG1 PE- or FITC-conjugated raised against trinitrophenol were used as iso-type controls to assess any nonspecific binding. U-937 (human histiocytic lyphoma) cells, from ATCC (Manassas, Va.) were harvested and centrifuged at 1000 rpm, 4° C., and washed twice in Dulbecco's PBS without Mg2+ or Ca2+ (DPBS, from Life Technologies) supplemented with 0.1% sodium azide (Sigma Chemicals) and 1% heat inactivated fetal bovine serum (washing buffer). 1×10$^6$ cells were aliquoted into Eppendorf tubes to a total volume of 100 $\mu$l in cell staining buffer (PBS without Mg or Ca, supplemented with 0.1% sodium azide, 1% heat inactivated fetal bovine serum and 5% mouse serum). The appropriate dilution of conjugated monoclonal antibody or conjugated iso-type control antibody was added to 1×10$^6$ cells (2.5 $\mu$l of CD11b or 20 $\mu$l of CD71 or CD82 were used according to the protocol supplied by the manufacturer), and the samples were incubated on ice, in the dark, for 60 min. Cells were then washed twice with washing buffer, fixed in 4% p-formaldehyde in PBS for 10 min, resuspended in washing buffer and analyzed by FACScan. FIGS. 6 and 7.

Although the invention has been described with reference to specific examples and embodiments, various changes, substitutions, and/or omissions may be made without departing from the spirit and scope of the invention defined in the appended claims.

What is claimed is:

1. A liposome having a lipid bilayer, said bilayer comprising an optically active ether lipid component, wherein said ether lipid is an anti-cancer agent, said ether lipid component being selected from the group consisting of an L-ether lipid, a D-ether lipid and an unequal mixture of an L-ether lipid and a D-ether lipid, and further comprising:

(a) an underivatized phosphatidylcholine;

(b) a sterol;

(c) about 5–20 mole % of a phosphatidylethanolamine linked to a dicarboxylic acid at the ethanolamine group of the phosphatidylethanolamine; and (d) wherein said liposome comprises greater than about 10 mole % to less than 30 mole % of said optically active ether lipid component, wherein said ether lipid stereoisomer is of the formula:

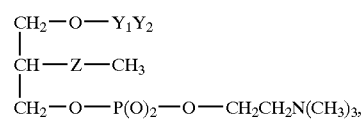

wherein Y$_1$ is $(CH_2)_{n1}(CH=CH)_n$ $(CH_2)_{n3}(CH=CH)_{n4}$ $(CH_2)_{n5}(CH=CH)_{n6}(CH_2)_{n7}$ $(CH=CH)_{n8}(CH_2)_{n9}$, the sum of n1+2n2+n3+2n4+n5+2n6+n7+2n8+n9 is an integer of from 3 to 23, n1 is zero or an integer of from 1 to 22, n3 is zero or an integer of from 1 to 19, n5 is zero or an integer of from 1 to 16, n7 is zero or an integer of from zero to 16, n9 is zero or an integer of from 1 to 10, and each of n2, n4, n6 and 8 is independently zero or 1;

$Y_2$ is $CH_3$ or $CO_2H$; and

Z is oxygen or sulfur.

2. The liposome of claim 1 wherein said liposome is unilamellar and has a diameter within the range of about 50–200 nm.

3. The liposome of claim 1, wherein the underivatized phosphatidylcholine is an unsaturated or partially unsaturated phosphatidylcholine.

4. The liposome of claim 3, wherein the underivatized phosphatidylcholine is dioleoyl phosphatidylcholine.

5. The liposome of claim 1, wherein the sterol is cholesterol.

6. The liposome of claim 1, wherein the phosphatidylethanolamine is selected from the group consisting of dipalmitoyl phosphatidylethanolamine, palmitoyloleoyl phosphatidylethanolamine and dioleoyl phosphatidylethanolamine.

7. The liposome of claim 6, wherein the phosphatidylethanolamine is dioleoyl phosphatidylethanolamine.

8. The liposome of claim 1, wherein the dicarboxylic acid is selected from the group consisting of glutaric acid, sebacic acid, succinic acid and tartaric acid.

9. The liposome of claim 8, wherein the dicarboxylic acid is glutaric acid.

10. The liposome of claim 1, wherein the phosphatidylethanolamine is dioleoyl phosphatidylethanolamine and the dicarboxylic acid is glutaric acid.

11. The liposome of claim 1, wherein $Y_2$ is $CH_3$, and Z is oxygen.

12. The liposome of claim 1, wherein the ether lipid has the formula:

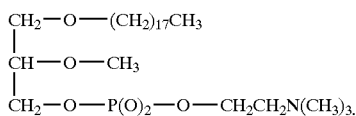

13. The liposome of claim 1, wherein the underivatized phosphatidylcholine is dioleoyl phosphatidylcholine, the sterol is cholesterol, the phosphatidylethanolamine is dioleolyl phosphatidylethanolamine, the dicarboxylic acid is glutaric acid and the ether lipid has the formula:

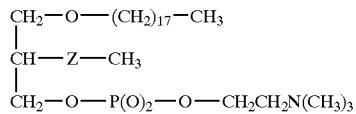

wherein Z is oxygen or sulfur.

14. The liposome of claim 13, wherein the bilayer comprises about 20 mole percent of the ether lipid, about 10 mole percent of the phosphatidylethanolamine linked to a dicarboxylic acid, about 30 mole percent cholesterol and about 40 mole percent dioleoyl phosphatidylcholine.

15. The liposome of claim 1, comprising an additional bioactive agent.

16. A pharmaceutical composition comprising a pharmaceutically acceptable carrier and an effective amount of the liposome of claim 1.

17. A method of treating a mammal afflicted with a cancer which comprises administering to the mammal an amount of the pharmaceutical composition of claim 18 comprising from about 0.1 mg of the ether lipid per kg of the body weight of the mammal to about 1000 mg per kg, wherein the cancer is selected from group consisting of lung cancers, brain cancers, colon cancers, ovarian cancers, breast cancers and leukemias.

18. The method of claim 17, comprising administering to the mammal an additional biologically active agent.

19. The method of claim 18, wherein the additional agent is selected from the group consisting of antineoplastic agents, antimicrobial agents, and hematopoietic cell growth stimulating agents.

20. The method of claim 17, wherein the liposome is a unilamellar liposome having a diameter of from about 50 nm to about 200 nm.

21. A method of treating a mammal afflicted with a cancer which comprises administering to the mammal an amount of the pharmaceutical composition of claim 16 comprising from about 0.1 mg of the ether lipid per kg of the body weight of the mammal to about 1000 mg per kg, wherein the cancer is selected from the group consisting of lymphomas, sarcomas and carcinomas.

22. The method of claim 21, comprising administering to the mammal an additional biologically active agent.

23. The method of claim 22, wherein the additional agent is selected from the group consisting of antineoplastic agents, antimicrobial agents, and hematopoietic cell growth stimulating agents.

24. The method of claim 21, wherein the liposome is a unilamellar liposome having a diameter from about 50 nm to about 200 nm.

* * * * *